US008380294B2

(12) United States Patent
Messier et al.

(10) Patent No.: US 8,380,294 B2
(45) Date of Patent: Feb. 19, 2013

(54) CARDIAC RISK STRATIFICATION

(75) Inventors: Marc D. Messier, Bombaye (BE); Daniel Becker, Heerlen (NL); Raphael Schneider, Maastricht (NL)

(73) Assignee: Medtronic, Inc., Minneapolis, MN (US)

( * ) Notice: Subject to any disclaimer, the term of this patent is extended or adjusted under 35 U.S.C. 154(b) by 357 days.

(21) Appl. No.: 12/765,482

(22) Filed: Apr. 22, 2010

(65) Prior Publication Data

US 2011/0082378 A1 Apr. 7, 2011

Related U.S. Application Data

(60) Provisional application No. 61/249,138, filed on Oct. 6, 2009.

(51) Int. Cl.
*A61B 5/0402* (2006.01)

(52) U.S. Cl. ....................................................... 600/513
(58) Field of Classification Search .................. None
See application file for complete search history.

(56) References Cited

U.S. PATENT DOCUMENTS

| | | | |
|---|---|---|---|
| 4,374,382 A | 2/1983 | Markowitz | |
| 5,117,824 A | 6/1992 | Keimel et al. | |
| 5,437,285 A | 8/1995 | Verrier et al. | |
| 5,545,186 A | 8/1996 | Olson et al. | |
| 5,749,900 A * | 5/1998 | Schroeppel et al. | 607/4 |
| 5,755,736 A | 5/1998 | Gillberg et al. | |
| 6,496,722 B1 | 12/2002 | Schmidt | |
| 6,920,360 B2 * | 7/2005 | Lee et al. | 607/60 |
| 7,079,887 B2 | 7/2006 | Burnes et al. | |
| 7,113,829 B2 * | 9/2006 | Lindberg et al. | 607/60 |
| 7,155,278 B2 | 12/2006 | King et al. | |
| 7,171,258 B2 | 1/2007 | Goode | |
| 7,181,277 B1 * | 2/2007 | Shelchuk et al. | 607/9 |
| 7,330,750 B2 | 2/2008 | Erkkila et al. | |
| 7,580,747 B1 | 8/2009 | Farazi et al. | |
| 2002/0138012 A1 | 9/2002 | Hodges et al. | |
| 2004/0186525 A1 * | 9/2004 | Burnes et al. | 607/17 |
| 2005/0234353 A1 | 10/2005 | Xue et al. | |
| 2006/0025838 A1 * | 2/2006 | Laufer et al. | 607/99 |
| 2007/0208266 A1 | 9/2007 | Hadley | |
| 2007/0244402 A1 | 10/2007 | Brockway et al. | |
| 2007/0255345 A1 | 11/2007 | Krause | |
| 2008/0033290 A1 * | 2/2008 | Saadat et al. | 600/433 |
| 2008/0319254 A1 * | 12/2008 | Nikolic et al. | 600/37 |
| 2008/0319332 A1 * | 12/2008 | Sornmo et al. | 600/513 |
| 2009/0234409 A1 * | 9/2009 | Shuros et al. | 607/17 |
| 2009/0275848 A1 * | 11/2009 | Brockway et al. | 600/513 |
| 2009/0281440 A1 * | 11/2009 | Farazi et al. | 600/510 |
| 2010/0016913 A1 * | 1/2010 | Arcot-Krishnamurthy et al. | 607/14 |

OTHER PUBLICATIONS

Schmidt et al., "Heart Rate Turbulence After Ventricular Premature Beats as a Predictor of Mortality After Acute Myocardial Infarction", Lancet, Apr. 24, 1999, vol. 353, Issue 9162, p. 1390.*
Wichterle et al., "Mechanisms Involved in Heart Rate Turbulence," Cardiac Electrophysiology Review 2002;6:262-266.
Savelieva et al., "QT-Interval Turbulence Induced by Atrial and Ventricular Extrastimuli in Patients with Ventricular Tachycardia," PACE vol. 28, Jan. 2005, Supplement 1, S187-S192.

(Continued)

*Primary Examiner* — Kennedy Schaetzle
(74) *Attorney, Agent, or Firm* — Michael C. Soldner

(57) ABSTRACT

This disclosure describes techniques for generating a risk stratification indicator based on HRT measurements computed using physiological parameters sensed by an implantable medical device (IMD). In some examples, the HRT measurements may be computed by the IMD based on the physiological parameters. In other examples, the IMD may sense the physiological parameters, and transmit data representative of the parameters to an external computing device, such as an IMD programmer, which then computes the HRT measurements. Exemplary physiological parameters include cardiac signals.

20 Claims, 8 Drawing Sheets

OTHER PUBLICATIONS

Vikman et al., "Heart Rate Turbulence After Atrial Premature Beats Before Spontaneous Onset of Atrial Fibrillation," JACC vol. 45, No. 2, Jan. 18, 2005, pp. 278-284.
Schmidt et al., "Heart-rate turbulence after ventricular premature beats as a predictor of mortality after acute myocardial infarction," The Lancet, vol. 353, Apr. 24, 1999, pp. 1390-1396.
Davies et al., "Relation of Heart Rate and Blood Pressure Turbulence Following Premature Ventricular Complexes to Baroreflex Sensitivity in Chronic Congestive Heart Failure," The American Journal of Cardiology, vol. 87, Mar. 15, 2001, pp. 737-742.
Grimm et al., "Prediction of Major Arrhythmic Events and Sudden Cardiac Death in Dilated Cardiomyopathy," Herz 25, No. 3, 2000, pp. 189-199.
Koyama et al., "Evaluation of Heart-Rate Turbulence as a New Prognostic Marker in Patients With Chronic Heart Failure," Circ. J. 2002; 66:902-907.
Iwasa, "Abnormal Heart Rate Turbulence Predicts the Initiation of Ventricular Arrhythmias," PACE vol. 28, pp. 1189-1197, Nov. 2005.
Grimm et al., "Heart-Rate Turbulence following Ventricular Premature Beats in Healthy Controls," A.N.E. vol. 8, No. 2, pp. 127-131, Apr. 2003.
Lindgren et al., "Heart Rate Turbulence after Ventricular and Atrial Premature Beats in Subjects without Structural Heart Disease," Journal of Cardiovascular Electrosphysiology, vol. 14, No. 5, May 2003, pp. 447-452.
Sestito et al., "Differences in Heart Rate Turbulence Between Patients With Coronary Artery Disease and Patients With Ventricular Arrhythmias But Structurally Normal Hearts," Am J. Cardiol., 2004;93:1114-1118.
Schwab et al., "Determinants of Heart Rate Turbulence after Ventricular Premature Beats in Healthy Volunteers," Hellenic J. Cardiol. 46:31-34, 2005.
Watanabe, "Heart Rate Turbulence Slope Reduction in Imminent Ventricular Tacharrhythmia and is Implications," J Cardiovasc. Electrophysiol., Jul. 2006, 17(7):735-740.
http://www.h-r-t.com/hrt/en/index.html, last updated Mar. 27, 2007, 1 pg.
http://www.h-r-t.org/hrt/en/publ_old.html, last updated Jun. 8, 2007, 35 pp.
U.S. Appl. No. 12/608,855, entitled "Arrhythmia Prediction Based on Heart Rate Turbulence," filed Oct. 29, 2009, by Lilian Kornet et al.
Medscape Today, "Time Domain Measures of HRV," J Cardiovasc Electrophysiol 2006; 17(6):691-694.
Stiles, "Carisma: Markers of Autonomic Function Stratify Post-Mi, Low-LVEF Sudden-Death Risk," found online at http://www.medscape.com/viewarticle556606, May 16, 2007, 2 pp.
Grimm, "Prognostic Significance of Heart Rate Turbulence Following Ventricular Premature Beats in Patients with Idiopathic Dilated Cardiomyopathy," Journal of Cardiovascular Electrophysiology, vol. 14 No. 8, pp. 819-824, Aug. 2003.
Huikuri et al., "Prediction of Fatal or Near-Fatal Ventricular Tachyarrhythmias in Patients with Depressed Left Ventricular Function after Acute Myocardial Infarction: The CARISMA Study," Medtronic Scientia, Sep. 2, 2007, 1 pg.
PowerPoint presentation by Thomsen et al., "Cardiac Arrhythmias and Risk Stratification in Patients with Low Ejection Fraction after Acute Myocardial Infarction: The CARISMA Study," presented at Heart Rhythm Society 2007 Scientific Sessions, May 10, 2007, 26 pp.
PowerPoint presentation by Thomsen et al., "CARISMA: Prognostic power of autonomic and electrophysiology measures of sudden-death risk," presented at Heart Rhythm Society 2007 Scientific Sessions, May 10, 2007, Denver CO., 1 pg.
Huikuri, "Recovery of Cardiac Autonomic Dysfunction after Acute Myocardial Infarction: a potential Predictor of Fatal or Near-Fatal Arrhythmic Events," abstract of presentation from 2008 American Heart Association conference, Nov. 8-12, 2008, 1 pg.
U.S. Appl. No. 61/122,029, filed Dec. 12, 2008.
Huikuri, "Attenuated recovery of heart rate turbulence early after myocardial infarction identifies patients at high risk for fatal or near-fatal arrhythmic events," Heart Rhythm 2010;7(2):229-35.

* cited by examiner

CARDIAC RISK STRATIFICATION

This application claims the benefit of U.S. Provisional Application No. 61/249,138, entitled, "CARDIAC RISK STRATIFICATION," and filed on Oct. 6, 2009, the entire contents of which being incorporated herein by reference.

TECHNICAL FIELD

The disclosure relates to implantable medical devices and, more particularly, implantable medical devices for analysis of cardiac function in a patient.

BACKGROUND

Medical devices, such as cardiac pacemakers, cardiac defibrillators, or implantable cardioverter-defibrillators, provide therapeutic electrical stimulation to a heart of a patient via electrodes carried by one or more medical leads and/or electrodes on a housing of the medical device. The electrical stimulation may include signals such as pulses or shocks for pacing, cardioversion or defibrillation. In some cases, a medical device may sense intrinsic depolarizations of the heart, and control delivery of stimulation signals to the heart based on the sensed depolarizations. Upon detection of an abnormal rhythm, such as bradycardia, tachycardia or fibrillation, an appropriate electrical stimulation signal or signals may be delivered to restore or maintain a more normal rhythm of the heart. For example, in some cases, an implantable medical device (IMD) or an external medical device may deliver pacing pulses to the heart of the patient upon detecting tachycardia or bradycardia or deliver cardioversion or defibrillation shocks to the heart upon detecting tachycardia or fibrillation.

SUMMARY

In general, this disclosure describes techniques for generating a risk stratification indicator based on an HRT measurement computed using physiological parameters sensed by an implantable medical device (IMD) or an external medical device. In some examples, the HRT measurement may be computed by an IMD based on the physiological parameters. In other examples, the IMD may sense the physiological parameters, and transmit data representative of the parameters to an external computing device, such as an IMD programmer, which then computes the HRT measurement and/or the risk stratification indicator. Exemplary physiological parameters include cardiac signals, which may be obtained, for example, from an electrocardiogram (ECG) or electrogram (EGM).

The IMD or external computing device may generate the risk stratification indicator based on the HRT measurement. The risk stratification indicator may calculate the risk of cardiac arrhythmia or mortality for the patient. In this manner, the patient can be classified into one of several cardiac arrhythmia or cardiac mortality risk strata. In some examples, the risk stratification indicator may prompt a clinician to prescribe new or additional cardiac therapy, such as implantation of an IMD or delivery of a drug, or to adjust existing therapy (e.g., cardiac therapy, spinal cord stimulation (SCS), and other types of neuro-modulation therapy), such as one or more parameters associated with electrical stimulation therapy or dosages associated with a drug.

In other examples, the IMD or external computing device may automatically generate an indicator based on the risk stratification indicator. The indicator may include, for example, an implantation indicator, which indicates that the patient is a candidate for implantation of an implantable therapy device, such as an implantable cardioverter/defibrillator (ICD), or an implantable drug delivery device. A patient may be considered a candidate for implantation of the device if the risk stratification indicator indicates, for example, that the patient is vulnerable and in need of the device or would generally benefit from the device in order to reduce cardiac arrhythmia or mortality risk. The IMD or external computing device may also initiate, cease, or adjust an existing cardiac therapy, e.g., delivered by the IMD or another device, e.g., a drug delivery device or a cardiac stimulation device separate from the IMD, based on the risk stratification indicator. In some examples, risk stratification may be based not only on the HRT measurement, but also other measurable or programmable information such as age, gender, cardiac indices such as QRS width, the standard deviation of all normal-to-normal RR intervals (SDNN), and left ventricular ejection fraction (LVEF), and history of heart failure or cardiac disease.

In one example, the disclosure is directed to a method comprising determining, from physiological parameters of the patient, a first heart rate turbulence (HRT) slope at a first time and a second HRT slope at a second time, calculating a difference value between the first slope and the second slope, and determining a level of recovery of autonomic function based on the calculated difference.

In another example, the disclosure is directed to an implantable medical device (IMD) comprising a measurement unit configured to obtain physiological parameters for a patient, and a processor configured to determine, from these parameters, a first heart rate turbulence (HRT) slope at a first time and a second HRT slope at a second time, calculate a difference value between the first slope and the second slope, and determine a level of recovery of autonomic function based on the calculated difference.

In another example, the disclosure is directed to a system comprising an implantable medical device (IMD) configured to obtain physiological parameters for a patient, and an external computing device configured to receive the physiological parameters, determine, from the physiological parameters, a first heart rate turbulence (HRT) slope at a first time and a second HRT slope at a second time, calculate a difference value between the first slope and the second slope, and determine a level of recovery of autonomic function based on the calculated difference.

In another example, the disclosure is directed to a computer-readable medium comprising instructions encoded on the computer-readable medium that, upon execution, cause a processor to determine, from physiological parameters of the patient, a first heart rate turbulence (HRT) slope at a first time and a second HRT slope at a second time, calculate a difference value between the first slope and the second slope, and determine a level of recovery of autonomic function based on the calculated difference.

In another example, the disclosure is directed to an implantable medical device (IMD) comprising means for determining, from physiological parameters of the patient, a first heart rate turbulence (HRT) slope at a first time and a second HRT slope at a second time, means for calculating a difference value between the first slope and the second slope, and means for determining a level of recovery of autonomic function based on the calculated difference.

In another example, the disclosure is directed to a method that comprises determining, from physiological parameters of the patient, a first heart rate turbulence (HRT) slope at a first time and a second HRT slope at a second time, comparing the first slope to a first threshold value and the second slope to a second threshold value, and determining a level of recovery of autonomic function based on the comparison.

In another example, the disclosure is directed to an implantable medical device (IMD) comprising a measurement unit configured to obtain physiological parameters for a patient, and a processor configured to determine, from physiological parameters of the patient, a first heart rate turbulence (HRT) slope at a first time and a second HRT slope at a second time, compare the first slope to a first threshold value and the second slope to a second threshold value, and determine a level of recovery of autonomic function based on the comparison.

In another example, the disclosure is directed to a system comprising an implantable medical device (IMD) configured to obtain physiological parameters for a patient, and an external computing device configured to receive the physiological parameters, determine, from physiological parameters of the patient, a first heart rate turbulence (HRT) slope at a first time and a second HRT slope at a second time, compare the first slope to a first threshold value and the second slope to a second threshold value, and determine a level of recovery of autonomic function based on the comparison.

In another example, the disclosure is directed to a computer-readable medium comprising instructions encoded on the computer-readable medium that, upon execution, cause a processor to determine, from physiological parameters of the patient, a first heart rate turbulence (HRT) slope at a first time and a second HRT slope at a second time, compare the first slope to a first threshold value and the second slope to a second threshold value, and determine a level of recovery of autonomic function based on the comparison.

In another example, the disclosure is directed to an implantable medical device (IMD) comprising means for determining, from physiological parameters of the patient, a first heart rate turbulence (HRT) slope at a first time and a second HRT slope at a second time, means for comparing the first slope to a first threshold value and the second slope to a second threshold value, and means for determining a level of recovery of autonomic function based on the comparison.

The details of one or more aspects of the disclosure are set forth in the accompanying drawings and the description below. Other features, objects, and advantages will be apparent from the description and drawings, and from the claims.

DETAILED DESCRIPTION

Autonomic markers such as heart rate turbulence (HRT) can be useful in analyzing cardiac function. HRT refers to the response of the sinus node to premature ventricular contractions (PVC). HRT provides a measure of the ability of a patient's autonomic control system to react to the disturbances in blood pressure caused by PVC. Healthy patients experience some degree of HRT. In some patients, reduced HRT may be an indicator of increased risk. As such, HRT may be used to predict the survival of a patient after an acute myocardial infarction (AMI).

Figure 1:
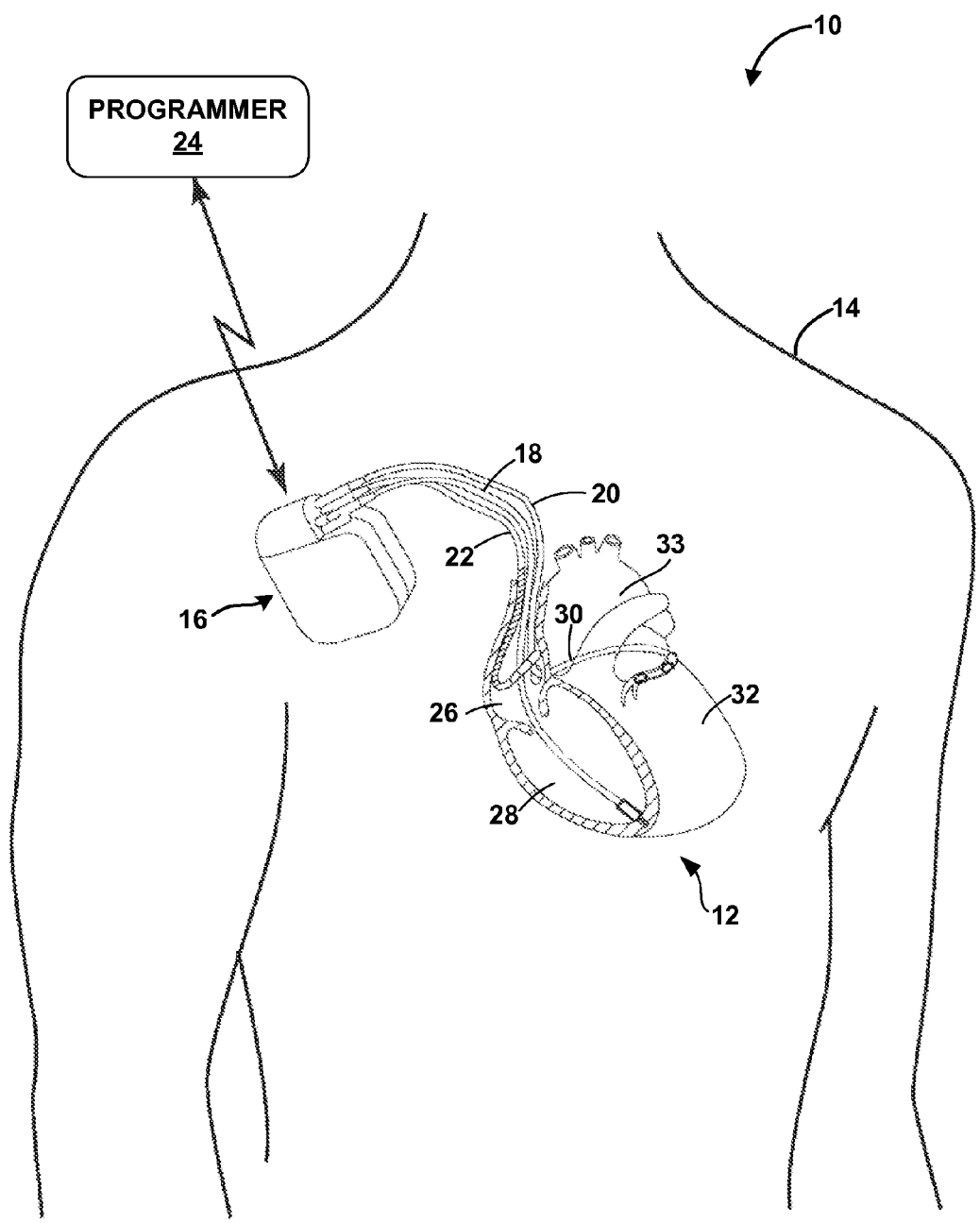
FIG. 1 is a conceptual diagram illustrating an example cardiac monitoring system.

FIG. 1 is a conceptual diagram illustrating an example monitoring system 10 that may be used to obtain a heart rate turbulence measurements (HRT) for a patient 14 and generate a risk stratification indicator based on the HRT measurements. The risk stratification indicator classifies a patient into one of a plurality of cardiac arrhythmia or cardiac mortality risk categories. Monitoring system 10 may obtain the HRT measurements based on detected physiological parameters of patient 14, such as cardiac signals of a heart 12 of patient 14. Patient 14 ordinarily, but not necessarily, will be a human. Monitoring system 10 includes an implantable medical device (IMD) 16, which is coupled to leads 18, 20, and 22, and a programmer 24. In some example configurations, monitoring system 10 may present with only an implantable medical device (IMD) 16, without leads, and programmer 24. In such a configuration, the leads may be replaced by a combination of casing electrodes.

IMD 16 may be referred to as an implantable monitor or an implantable loop recorder (ILR). IMD 16 may be, for example, an implantable cardiac monitor that does not provide therapy (e.g., stimulation therapy) to patient 14. In this case, the ILR may be used to generate a risk stratification indicator to determine whether the patient is a candidate for implantation of an implantable therapy device, such as a cardiac pacemaker, an implantable cardioverter-defibrillator (ICD), or a cardiac resynchronization therapy (CRT) pacing device. Hence, in some examples, an ILR may be used in patient 14 in advance of implantation of a stimulation therapy device to determine whether implantation of a stimulation therapy device would be advisable for the patient. In other examples, an ILR may be used in conjunction with an implantable cardiac pacemaker, e.g., within the same IMD as the ILR or in a different IMD, to determine whether patient 14 may benefit from implantation of an ICD. An ILR may sense, store, and process electrical activity of the heart. It should be noted that such a system configuration does not require leads. Rather, in some example configurations, electrodes may be placed on the housing of the device (referred to throughout this disclosure as "can electrodes," "case electrodes," or "housing electrodes"). In still other examples, e.g., as described with respect to FIGS. 2 and 4, IMD 16 may be incorporated in an implantable medical device that delivers electrical stimulation to heart 12 of patient 14. Examples of IMDs for delivery of electrical stimulation include a cardiac pacemaker, an ICD, or a CRT device, each of which provides electrical stimulation pulses and/or shocks to heart 12 via electrodes coupled to one or more leads.

Leads 18, 20, 22 extend into the heart 12 of patient 14 to sense electrical activity of heart 12. In the example shown in FIG. 1, right ventricular (RV) lead 18 extends through one or more veins (not shown), the superior or inferior vena cava (not shown), and right atrium 26, and into right ventricle 28. Left ventricular (LV) coronary sinus lead 20 may extend through one or more veins, the vena cava, right atrium 26, and into the coronary sinus 30 to a region adjacent to the free wall of the surface of the left ventricle 32 of heart 12. Right atrial (RA) lead 22 extends through one or more veins and the vena cava, and into the right atrium 26 of heart 12.

IMD 16 may sense electrical signals attendant to the depolarization and repolarization of heart 12 via case electrodes only (not shown in FIG. 1) or coupled to at least one of the leads 18, 20, 22. The configurations of electrodes used by IMD 16 for sensing may be unipolar (e.g., using a lead electrode and a can electrode) or bipolar (e.g., using two lead electrodes or two can electrodes). IMD 16 may collect, for example, cardiac signals in the form of an electrogram (EGM), which may be used to determine a heart rate interval (e.g., R-R interval) to calculate HRT measurements.

In some examples, programmer 24 may be a handheld computing device or a computer workstation. Programmer 24 may include a user interface that receives input from a user. The user interface may include, for example, a keypad and a display, which may for example, be a cathode ray tube (CRT) display, a liquid crystal display (LCD) or light emitting diode (LED) display. The keypad may take the form of an alphanumeric keypad or a reduced set of keys associated with particular functions. Programmer 24 can additionally or alternatively include a peripheral pointing device, such as a mouse, via which a user may interact with the user interface. In some examples, a display of programmer 24 may include a touch screen display, and a user may interact with programmer 24 via the display.

A user, such as patient 14, a physician, technician, or other clinician, may interact with programmer 24 to communicate with IMD 16. For example, the user may interact with programmer 24 to retrieve physiological or diagnostic information from IMD 16. A user may also interact with programmer 24 to program IMD 16, e.g., to select values for operational parameters of the IMD 16.

For example, a user such as a clinician may use programmer 24 to retrieve information from IMD 16 regarding the rhythm of heart 12 (e.g., occurrences of PVC and R-R intervals) and trends therein over time. As another example, the user may use programmer 24 to retrieve information from IMD 16 regarding the performance or integrity of IMD 16 or other components of system 10, such as leads 18, 20, and 22, or a power source of IMD 16. In some examples, programmer 24 may also receive alerts from IMD 16, such as an alert generated in response to a risk stratification indicator when HRT measurements obtained by IMD 16 indicate increased risk to patient 14, as will be described in more detail.

IMD 16 and programmer 24 may communicate via wireless communication using any techniques known in the art. Examples of communication techniques may include, for example, low frequency or radiofrequency (RF) telemetry, but other techniques are also contemplated. In some examples, programmer 24 may include a programming head that may be placed proximate to the body of patient 14 near the IMD 16 implant site in order to improve the quality or security of communication between IMD 16 and programmer 24.

IMD 16 may utilize the cardiac signals detected by electrodes carried by one or more of leads 18, 20, 22 to determine cardiac measurements such as HRT. IMD 16 or programmer 24 may then generate the risk stratification indicator based on the HRT measurement, as will be described in further detail below. HRT provides a measure of the ability of a patient's autonomic control system to react to the disturbances in blood pressure caused by a PVC. HRT may be characterized by two values: turbulence onset and turbulence slope. The heart rate preceding a PVC and the heart rate following the PVC are used to identify turbulence onset, i.e., the start of turbulence. Turbulence slope may be measured as the slope, e.g., the steepest slope, of a linear regression line for each sequence of a number of consecutive R-R intervals, e.g., five, following a normal heartbeat after identification of a PVC and onset of turbulence. Typically, heart rate increases after a PVC to a rate greater than what the heart rate was prior to the PVC. Then, the heart rate decreases to a rate below what the heart rate was prior to the PVC, before returning to the rate prior to the PVC. In patients with increased risk of heart failure, HRT is weak or even non-existent. That is, a low heart rate turbulence slope measurement may reflect an impaired autonomic response and an increased risk of heart failure.

Because HRT measurements may correlate to heart failure of patient 14, IMD 16 or programmer 24 may utilize the HRT measurements to generate a risk stratification indicator for patient 14. In accordance with one example technique of the present invention, a risk stratification indicator may be generated based on the difference between HRT slopes over time. The risk stratification indicator may indicate the risk of having future cardiac arrhythmias or cardiac mortality for patient 14. In some cases, the risk stratification indicator may serve to classify the patient 14 among two or more different risk strata, i.e., cardiac/non-cardiac mortality or cardiac arrhythmia vulnerability risk categories, each of which may be correlated with candidacy for IMD implantation, or with modification of existing therapy (e.g., cardiac therapy, spinal cord stimulation (SCS), and other types of neuro-modulation therapy), and more general medical interventions.

For example, as will be described in further detail below, IMD 16 or programmer 24 may automatically generate an implantation indicator based on generation of the risk stratification indicator, or based on a value of the risk stratification indicator. In either case, the risk stratification indicator may provide an indication that patient 14 is a candidate for implantation of an implantable therapy device, such as a cardiac pacemaker, an implantable cardioverter-defibrillator (ICD), a cardiac resynchronization therapy (CRT) pacing device, neuro-modulation device, or a drug delivery device. A clinician may act on the implantation indicator as a recommendation, and elect to proceed with implantation of an IMD in patient 14. In general, a patient may be considered a candidate for implantation of the device if the risk stratification indicator indicates that the patient is in a state of arrhythmic vulnerability, and critically in need of the device or would benefit from the device in order to reduce cardiac arrhythmia or cardiac mortality risk.

Alternatively, instead of generating an automatic implantation indicator, a clinician may review the risk stratification indicator and use the risk stratification indicator in a broader clinical sense, to determine whether patient 14 is a candidate for implantation of one of the implantable therapy devices, or whether to prescribe a drug to the patient 14. As a further alternative, the risk stratification indicator may be used by IMD 16, programmer 24, or a clinician to prescribe adjustment of an existing cardiac therapy, such as one or more parameters associated with cardiac electrical stimulation therapy or dosages associated with one or more drugs. In other examples, the risk stratification indicator may be used by an implantable drug delivery device to prescribe adjustment of an existing drug delivery therapy. IMD 16 or programmer 24 may also generate an alert to a user, such as patient 14 or a clinician, based on the risk stratification indicator. The alert may indicate that the condition of patient 14 is changing or has changed.

In some examples, the risk stratification indicator may comprise a binary output, classifying the patient into one of two cardiac arrhythmia or cardiac mortality risk categories, such as risk or no risk, or high risk or low risk, or one of a plurality of risk levels corresponding to three or more cardiac arrhythmia or cardiac mortality risk categories (e.g., low risk, medium risk, high risk or very low risk, low risk, medium risk, high risk or very high risk). In turn, IMD 16 or programmer 24 may automatically generate, based on HRT slope difference over time, for example, a binary implant indicator such as implant or no implant, or a range of implant indicators such as implant critically needed, patient would benefit from implant, implant not needed but may be beneficial, implant not needed but optional, or no implant benefit likely. Hence, IMD 16 or programmer 24 may generate different implant indications for presentation to a clinician or other user for different, corresponding values of the risk stratification indicator.

IMD 16 includes leads 18, 20, 22, which carry electrodes that measure cardiac signals, and may thus obtain continuous or chronic HRT measurements. This may provide the ability to monitor a condition of patient 14 in between clinical visits, and may also enable IMD 16, programmer 24, or another computing device to produce trends of the HRT measurements over time, which may indicate a change in the condition of patient 14, and a progression of heart failure in the patient.

Figure 2:
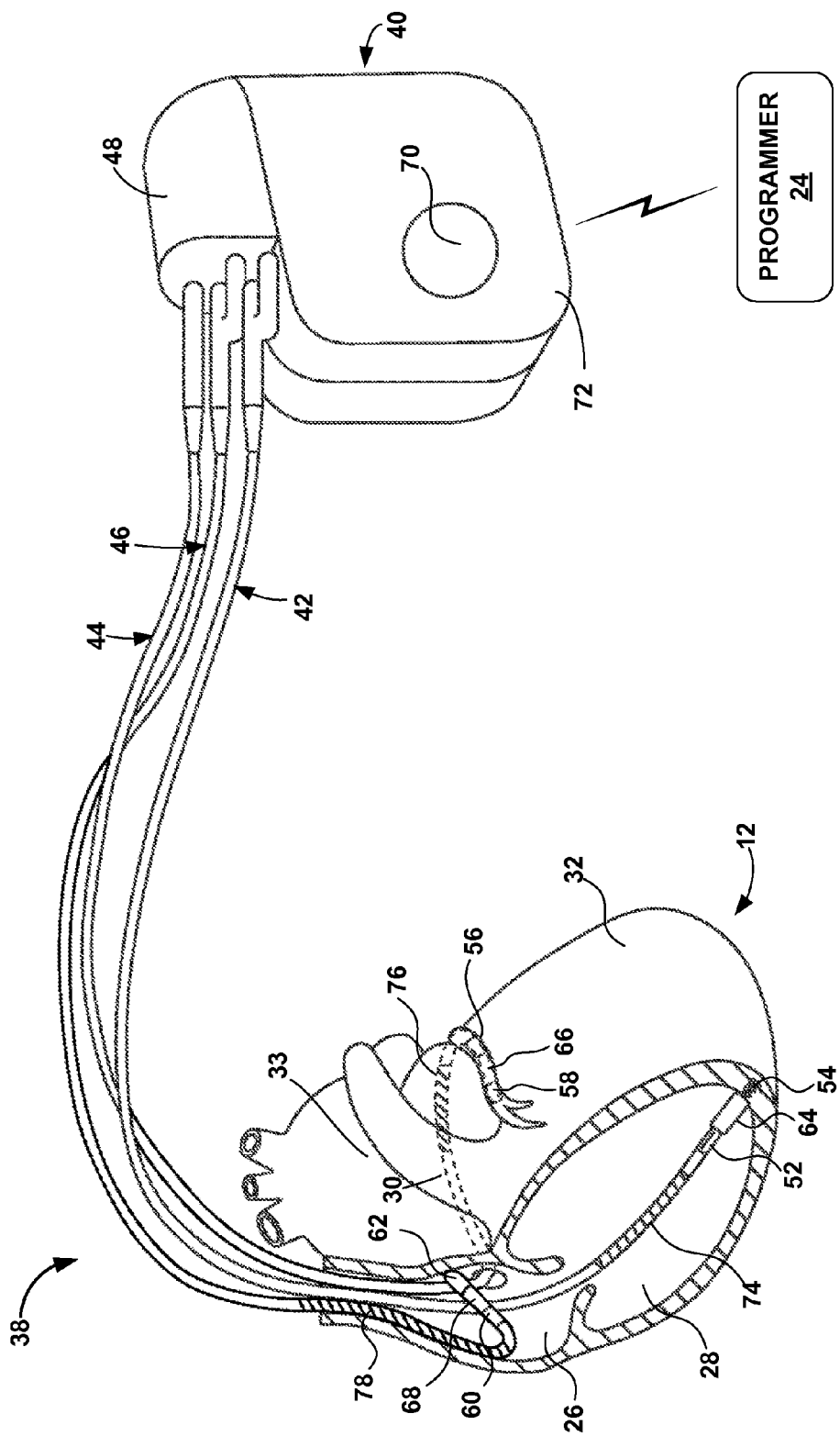
FIG. 2 is a conceptual diagram illustrating an example cardiac therapy system.

FIG. 2 is a conceptual diagram illustrating an exemplary therapy system 38, including programmer 24, an IMD 40 and leads 42, 44, 46. Leads 42, 44, 46 may be electrically coupled to an electrical stimulation generator, a sensing module, or other modules of IMD 40 via connector block 48. In some examples, proximal ends of leads 42, 44, 46 may include electrical contacts that electrically couple to respective electrical contacts within connector block 48. In addition, in some examples, leads 42, 44, 46 may be mechanically coupled to connector block 48 with the aid of set screws, connection pins or another suitable mechanical coupling mechanism.

Each of the leads 42, 44, 46 includes an elongated insulative lead body, which may carry a number of concentric coiled conductors separated from one another by tubular insulative sheaths. In the illustrated example, bipolar electrodes 52 and 54 are located proximate to a distal end of lead 42. In addition, bipolar electrodes 56 and 58 are located proximate to a distal end of lead 44 and bipolar electrodes 60 and 62 are located proximate to a distal end of lead 46.

Electrodes 52, 56, and 60 may take the form of ring electrodes, and electrodes 54, 58 and 62 may take the form of extendable helix tip electrodes mounted retractably (or not retractably) within insulative electrode heads 64, 66 and 68, respectively. Each of the electrodes 52, 54, 56, 58, 60 and 62 may be electrically coupled to a respective one of the coiled conductors within the lead body of its associated lead 42, 44, 46, and thereby coupled to respective ones of the electrical contacts on the proximal end of leads 42, 44 and 46.

Electrodes 52, 54, 56, 58, 60 and 62 may sense electrical cardiac signals attendant to the depolarization and repolarization of heart 12. The cardiac signals are conducted to IMD 40 via the respective leads 42, 44, 46. In the example of FIG. 2, IMD 40 also may deliver pacing pulses via electrodes 52, 54, 56, 58, 60 and 62 to cause depolarization of cardiac tissue of heart 12. In some examples, as illustrated in FIG. 2, IMD 40 includes one or more housing electrodes, such as housing electrode 70, which may be formed integrally with an outer surface of hermetically-sealed housing 72 of IMD 40 or otherwise coupled to housing 72. In some examples, housing electrode 70 is defined by an uninsulated portion of an outward facing portion of housing 72 of IMD 40. Other divisions between insulated and uninsulated portions of housing 72 may be employed to define two or more housing electrodes. In some examples, housing electrode 70 comprises substantially all of housing 72. Any of the electrodes 52, 54, 56, 58, 60 and 62 may be used for unipolar sensing or pacing in combination with housing electrode 70. As described in further detail with reference to FIG. 4, housing 72 may enclose a stimulation generator that generates cardiac pacing pulses or pre-defined sequences of pulses (e.g., a train of pulses), or waveforms and defibrillation or cardioversion shocks, as well as a cardiac sensing module for monitoring the rhythm and other attributes of heart 12.

Leads 42, 44, and 46 also include elongated electrodes 74, 76, 78, respectively, which may take the form of a coil. IMD 40 may deliver cardioversion and/or defibrillation shocks to heart 12 via any combination of elongated electrodes 74, 76, 78, and housing electrode 70. Electrodes 74, 76, 78 may be fabricated from any suitable electrically conductive material, including, but not limited to, platinum, a platinum alloy or other materials known to be usable in implantable defibrillation electrodes.

Similar to IMD 16, IMD 40 may obtain HRT measurements by detecting variation in the intrinsic pulse rate (e.g., R-R interval) of heart 12. IMD 40 or programmer 24 may use the HRT measurements to generate a risk stratification indicator. Again, the risk stratification indicator may indicate the risk of cardiac arrhythmia or cardiac mortality to patient 14, and may categorize the patient into one of two or more risk categories for cardiac arrhythmia or mortality (e.g., low risk, medium risk, high risk). The risk stratification indicator may be presented to a user such as a clinician via programmer 24 or another computing device to permit the clinician to quickly ascertain the cardiac arrhythmia or cardiac mortality risk status of the patient, and consider an appropriate course of action, such as implantation of a cardiac electrical stimulation therapy device, stents, valves, modified medication, and other medical interventions.

Based on the risk stratification indicator, in some examples, IMD 40 or programmer 24 may automatically generate an instruction to initiate or modify a therapy program according to which IMD 40 delivers stimulation to heart 12. For example, the IMD 40 or programmer 24 may initiate resetting or suspension of the current therapy program by IMD 40 based on the risk stratification indicator, or may direct IMD 40 to switch to a different therapy program based on the risk stratification indicator. Each therapy program may define a plurality of stimulation parameters, including, for example, stimulation pulse width, stimulation pulse amplitude, stimulation frequency, an electrode configuration and/or polarity, pacing mode switch for single, dual, and triple chambers, for leads A, V, RV and/or LV, or the like.

IMD 40 of programmer 24 may also generate an alert to a user, such as patient 14 or a clinician, based on the risk stratification indicator. The alert may comprise a notification that the condition of patient 14 is changing or has changed. Again, in some examples, the risk stratification indicator may comprise a binary output, such as risk or no risk, or high risk or low risk, or may comprise one of a plurality of risk levels (e.g., very low risk, medium risk, high risk). In this manner, the risk stratification indicator may categorize the patient into one of two or more cardiac arrhythmia or cardiac mortality risk categories for convenient interpretation by a clinician. For example, in contrast to raw HRT values, the risk categories may be expressed textually (e.g., low, medium, high, or mild-/severe risk of cardiac arrhythmia, or cardiac/any mortality) to permit ready interpretation, in a simple numeric format (e.g., 1, 2, 3 or A, B, C), or in a color-coded format (e.g., green, yellow, red).

In some examples, IMD 16 or programmer 24 may generate the risk stratification indicator based on the HRT measurements in combination with one or more of an age of patient 14, gender of patient 14, history of heart failure or cardiac disease of patient 14, measurable and programmable cardiac indices such as QRS width, SDNN and LVEF, or the like.

The configurations of monitoring system 10 illustrated in FIG. 1 and therapy system 38 illustrated in FIG. 2 are merely two examples. In other examples, a monitoring system or therapy system may include epicardial leads and/or patch electrodes instead of, or in addition to, the transvenous leads 18, 20, 22, 42, 44, 46 illustrated in FIGS. 1 and 2.

In other examples of therapy systems that provide electrical stimulation therapy to heart 12, a therapy system may include any suitable number of leads coupled to IMD 40, and each of the leads may extend to any location within or proximate to heart 12. For example, other examples of therapy systems may include three transvenous leads located as illustrated in FIGS. 1 and 2, and an additional lead located within or proximate to left atrium 33. As another example, other examples of therapy systems may include a single lead that extends from IMD 16 into right atrium 26 or right ventricle 28, or two leads that extend into a respective one of the right ventricle 26 and right atrium 28.

Figure 3:
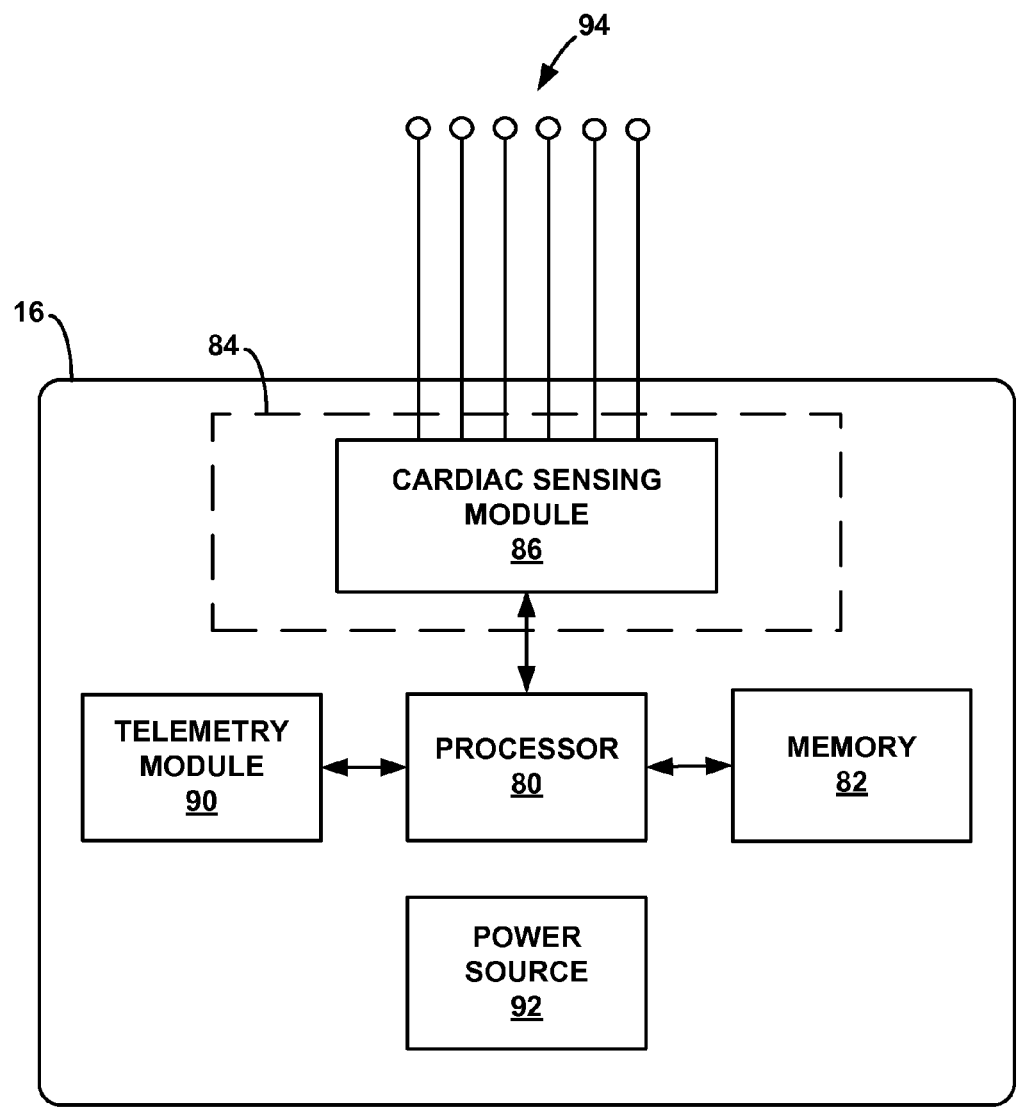
FIG. 3 is a functional block diagram of an example implantable medical device that monitors a cardiac signal.

FIG. 3 is a functional block diagram of one example configuration of IMD 16, which includes a processor 80, memory 82, a measurement unit 84, a telemetry module 90, and a power source 92. In the example of FIG. 3, measurement unit 84 includes a cardiac sensing module 86.

Memory 82, a computer-readable medium, includes computer-readable instructions that, when executed by processor 80, cause IMD 16 and processor 80 to perform various functions attributed to IMD 16 and processor 80 herein. Memory 82 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, magneto-resistive random access memory (MRAM), or any other digital media.

Processor 80 may include any one or more of a microprocessor, a controller, a digital signal processor (DSP), an application specific integrated circuit (ASIC), a field-programmable gate array (FPGA), or equivalent discrete or integrated logic circuitry. In some examples, processor 80 may include multiple components, such as any combination of one or more microprocessors, one or more controllers, one or more DSPs, one or more ASICs, or one or more FPGAs, as well as other discrete or integrated logic circuitry. The functions attributed to processor 80 herein may be embodied as software, firmware, hardware or any combination thereof.

Measurement unit 84 may obtain an HRT measurement by detecting one or more physiological parameters of patient 14. For example, in the example illustrated in FIG. 3, measurement unit 84 includes a cardiac sensing module 86, which detects a cardiac signal of heart 12.

Cardiac sensing module 86 may detect cardiac signals via at least one of a plurality of electrodes 94 in order to monitor electrical activity of heart 12, e.g., by constructing an electrogram (EGM) from the cardiac signals. Electrodes 94 may be dedicated sensing electrodes if IMD 16 is configured as a physiological signal monitoring device. Alternatively, electrodes 94 may form dedicated sensing electrodes or combined sensing/stimulation electrodes in examples in which IMD 16 is configured to also deliver electrical stimulation. Cardiac sensing module 86 may also include a switch module (not shown) to select which of the available electrodes 94 are used to sense the cardiac activity. In some examples, processor 80 may select the electrodes 94 that function as sense electrodes via the switch module within cardiac sensing module 86, e.g., by providing signals via a data/address bus. In some examples, cardiac sensing module 86 includes one or more sensing channels, each of which may comprise an amplifier. In response to the signals from processor 80, the switch module within cardiac sensing module 86 may couple the outputs from the selected electrodes to one of the sensing channels.

In some examples, one channel of cardiac sensing module 86 may include an amplifier that receives signals from electrodes 94, which may be used for sensing R-waves in right ventricle 28 of heart 12. Another channel may include another amplifier that receives signals from electrodes (not shown) that are used for R-wave sensing proximate to left ventricle 32 of heart 12. In some examples, the amplifiers may each take the form of an automatic gain controlled amplifier that provides an adjustable sensing threshold as a function of the measured R-wave amplitude of rhythm of heart 12. The amplifiers and corresponding sensing channels of sensing module 86 detect PVCs and R-waves for use in establishing an R-R interval for the heart of patient 14. The R-R interval indicates the time between successive ventricular depolarizations, either involving the whole heart as an organ, in addition to, or more precisely in, the right ventricle or in the left ventricle. The R-R interval indicates the cardiac cycle length, which may be converted to express heart rate in terms of beats per minute. As will be described in more detail below, the R-R interval may be used to calculate HRT and, in particular, turbulence slope.

In some examples, cardiac sensing module 86 includes a channel that comprises an amplifier with a relatively wider pass band than the R-wave sensing amplifier(s). Signals from the selected sensing electrodes that are selected for coupling to this wide-band amplifier may be provided to a multiplexer, and thereafter converted to multi-bit digital signals by an analog-to-digital converter for storage in memory 82 as an EGM. In some examples, the storage of such EGMs in memory 82 may be under the control of a direct memory access circuit. Processor 80 may employ digital signal analysis techniques to characterize the digitized signals stored in memory 82 to detect and classify the rhythm of heart 12 from the cardiac signals. Processor 80 may detect and classify the rhythm of heart 12 by employing any of the numerous signal processing methodologies known in the art.

For example, processor 80 may determine the R-R interval from the cardiac signal obtained from the wide-band amplifier channel or the R-wave detections provided by the R-wave amplifier channels. Again, the R-R interval is the length of time between consecutive R-waves, i.e., ventricular depolarizations, and represents the cardiac cycle length. In some examples, processor 80 may determine an R-R interval for each of a plurality of consecutive R-waves, and may store the R-R intervals in memory 82. Processor 80 may use one or more of the determined R-R intervals in determining the HRT measurements.

Processor 80 may determine the HRT measurement and, in particular, the turbulence slope, based on the cardiac signals detected by cardiac sensing module 86 via electrodes 94. For example, after cardiac sensing module 86 detects a PVC, R-wave amplifier channels detect subsequent R-waves. Processor 80 may then determine R-R intervals for a number (e.g., fifteen) of normal cardiac cycles following the PVC. Then, processor 80 may determine one or more linear regression lines through any five consecutive R-R intervals. Processor 80 may then calculate the slope of each linear regression line(s) determined. The slope(s) calculated are heart rate turbulence slopes, and the steepest slope may be stored in memory, e.g., memory 82, as a first turbulence slope.

In accordance with techniques of this disclosure, the first turbulence slope is calculated over an interval of time (e.g., 24 hours) at a first time after a myocardial infarction (e.g., about 1 week). Over an interval of time (e.g., 24 hours) at a second time, the second time being after the first time and following the myocardial infarction (e.g., about 6 weeks), a second turbulence slope is calculated by processor 80. The first time may be in a range of time following a myocardial infarction, e.g., 3 days to 21 days, more preferably 5 days to 14 days, and even more preferably about 7 days after the myocardial infarction. The second time may be in a range of time after the first time and following the myocardial infarction, e.g., 4 weeks to 10 weeks, more preferably 5 weeks to 8 weeks, and even more preferably about 6 weeks after the myocardial infarction. As previously mentioned, turbulence slope may be measured as the slope, e.g., the steepest slope, of a linear regression line for each sequence of a number of consecutive R-R intervals, e.g., five, following a normal heartbeat after identification of a PVC and onset of turbulence. The slope is measured over time intervals, e.g., 24 hours, which are generally coincident with the first and second times.

After cardiac sensing module 86 detects a PVC at a second time, e.g., at about day 42 or about 6 weeks after the myocardial infarction, R-wave amplifier channels detect subsequent R-waves. Processor 80 may then determine R-R intervals for a number (e.g., fifteen) of normal cardiac cycles following the PVC. Then, processor 80 may determine one or more linear regression lines through any five consecutive R-R intervals. Processor 80 may then calculate the slope of each linear regression line(s) determined. The steepest slope may be stored in memory, e.g., memory 82, as a second turbulence slope. Following calculation of the second turbulence slope, processor 80 may calculate the difference between the first turbulence slope determined at a first time, e.g., at about one week following an acute myocardial infarction, and the second turbulence slope determined at a second time, e.g., at about six weeks following the acute myocardial infarction (e.g., second turbulence slope minus first turbulence slope, or change (Δ) in HRT slope between the first time and the second time), and store the difference in turbulence slope in memory 82, for example. In some examples, processor 80 may then compare the difference in turbulence slope to a threshold value, e.g., stored in memory 82, in order to determine the risk stratification indicator. In one example, the threshold value is about 2 milliseconds (ms) per R-R interval. By way of specific example, assume that the first turbulence slope is 14 ms per R-R interval and the second turbulence slope is 17 ms per R-R interval. The difference between the second and the first turbulence slopes is 3 ms per R-R interval. The difference between the second and the first turbulence slopes is then compared to a threshold value, e.g., about 2 ms per R-R interval.

If the difference in slope is less than the threshold value of about 2 ms per R-R interval, indicating a possible lack of autonomic recovery, processor 80 may execute instructions that cause a binary value of 1 to be output, indicating that the patient is at risk, i.e., has a higher risk of ventricular tachycardia or ventricular fibrillation, for example. In other words, if the change in HRT slope is too low, then the patient's autonomic response has not recovered sufficiently after the myocardial infarction. As such, the patient is still at risk of another myocardial infarction. But, a larger change in HRT slope may indicate healing/restoration of the heart function, and as such, the patient is less at risk of another myocardial infarction. A binary value of 1 may result in processor 80 generating an alert to a clinician, for example. If the difference in slope is equal to or greater than about 2 ms per R-R interval, processor 80 may execute instructions that cause a binary value of 0 to be output, indicating that the patient is not at risk.

Processor 80 may then generate, for example, an alert to a user, such as patient 14 or a clinician, based on the risk stratification indicator, e.g., the binary value generate by processor 80. In other examples, processor 80 may generate based on the risk stratification indicator an indicator that patient 14 is a candidate for an IMD that provides therapy, such as stimulation therapy or drug delivery, or an indicator that contemporary prescribed therapy, such as stimulation therapy or drug delivery, should be adjusted. The risk stratification indicator may comprise a binary output (e.g., risk or no risk or high risk or low risk), or one of a plurality of risk levels (e.g., very low risk, medium risk, high risk), in which case multiple thresholds for each category may be utilized as described below.

It should be noted that, in some examples, if there is no intrinsic PVC to detect, a PVC may be induced in the patient so that HRT may be calculated in the manner described above. HRT assesses the response of the autonomic nervous system to a PVC, whether the PVC is intrinsic or induced, e.g., stimulated. If the IMD is a pacemaker or an ICD, the IMD may induce a heart activity by sending an electrical stimulus. Normally, this stimulus is delivered if a normal heartbeat does not occur. The IMD, however, may be programmed to deliver a stimulus only to a ventricle and thus induce a PVC, which then allows HRT parameters to be calculated. For example, the IMD may deliver, when no intrinsic abnormal heartbeats are occurring, electrical stimulation at a first time in order to induce a plurality of abnormal heartbeats at the first time and deliver electrical stimulation at a second time in order to induce a plurality of abnormal heartbeats at the second time. The heart rate turbulence parameters, e.g., the HRT slope, may be determined from the induced abnormal heartbeats.

Telemetry module 90 includes any suitable hardware, firmware, software, or any combination thereof for communicating with another device, such as programmer 24 (FIG. 1). Under the control of processor 80, telemetry module 90 may receive downlink telemetry from and send uplink telemetry to programmer 24 with the aid of an antenna, which may be internal and/or external. Processor 80 may provide the data to be uplinked to programmer 24 and the control signals for the telemetry circuit within telemetry module 86, e.g., via an address/data bus. In some examples, telemetry module 90 may provide received data to processor 80 via a multiplexer.

In some examples, processor 80 may transmit atrial and/or ventricular cardiac signals (e.g., EGM signals) produced by atrial and/or ventricular sense amplifier circuits within cardiac sensing module 86 to programmer 24. Programmer 24 may interrogate IMD 16 to receive the cardiac signals. Processor 80 may store the cardiac signals within memory 82, and retrieve stored cardiac signals from memory 82. Processor 80 may also generate and store marker channel codes indicative of different cardiac episodes, e.g., PVCs, that cardiac sensing module 86 or processor 80 detects, and transmit the marker codes to programmer 24. An example pacemaker with marker-channel capability is described in U.S. Pat. No. 4,374,382 to Markowitz, entitled, "MARKER CHANNEL TELEMETRY SYSTEM FOR A MEDICAL DEVICE," which issued on Feb. 15, 1983 and is incorporated herein by reference in its entirety.

In other examples, processor 80 may transmit parametric data derived from atrial and/or ventricular cardiac signals produced by cardiac sensing module 86 to programmer 24. In particular, processor 80 may transmit R-R interval data and selective R-R' difference data, for example. Hence, in various implementations, processor 80 may generate HRT indicators and a risk stratification indicator within IMD 16, or transmit raw data, processed data or parametric data to programmer 24 for generation of HRT risk stratification indicators. Processed data may include, for example, particular values such as Q-R and R-S peak heights, QRS widths or widths at mid height. Processed data may also include, for example, R to the next R (R-R') peak ratios or width ratios, where R is a normal, or reference, beat and R' is an abnormal beat, e.g., the beat qualifies as a premature beat. Processed data may further include, for example, the difference between sequential R-R' interval durations when both R and R' are normal intervals, which may be used for example for SDNN calculations. Parametric data may include particular intervals or values, or information such as marker channel data useful in determining intervals or values.

The various components of IMD 16 may be coupled to power source 92, which may include a rechargeable or non-rechargeable battery and suitable power supply circuitry. A non-rechargeable battery may be selected to last for several years, while a rechargeable battery may be inductively charged from an external device, e.g., on a daily or weekly basis.

Although FIG. 3 illustrates cardiac sensing module 86 as a separate component from processor 80, in other examples, processor 80 may include some of the functionality attributed to cardiac sensing module 86 in this disclosure. For example, cardiac sensing module 86 shown in FIG. 3 may include software executed by processor 80. If cardiac sensing module 86 includes firmware or hardware, cardiac sensing module 86 may be a separate one of the one or more processors 80 or may be a part of a multifunction processor. As previously described, processor 80 may comprise one or more processors.

Further, in other examples of monitoring system 10 or therapy system 38, cardiac sensing module 86 may be separate from IMD 16, 40. That is, although cardiac sensing module 86 is shown in FIG. 3 to be incorporated within or coupled to a housing of IMD 16 along with other components such as processor 80, in other examples, cardiac sensing module 86 may be enclosed in a separate housing. A stand-alone cardiac sensing module that is enclosed in a separate housing from the housing of IMD 16 may be mechanically coupled to IMD 16 or may be mechanically decoupled from IMD 16. For example, in some examples, cardiac sensing module 86 may be implanted within patient 14 at a separate location from IMD 16 and leads 18, 20, 22. Cardiac sensing module 86 may communicate with IMD 16 via a wired connection or via wireless communication techniques, such as RF telemetry.

Figure 4:
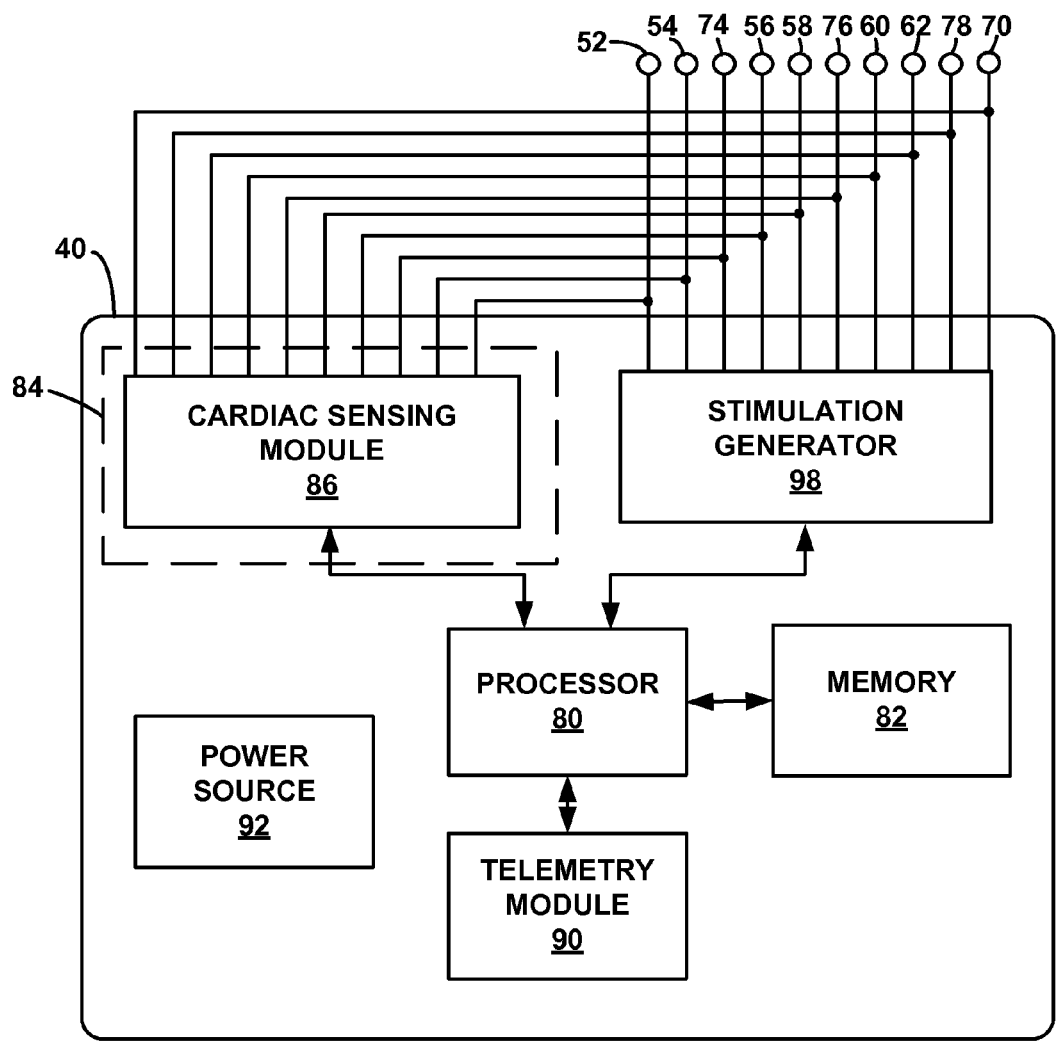
FIG. 4 is a functional block diagram of an example implantable medical device that monitors a cardiac signal and provides stimulation therapy to a heart.

FIG. 4 is a functional block diagram of one example configuration of IMD 40, which includes processor 80, memory 82, measurement unit 84 including cardiac sensing module 86, telemetry module 90, power source 92, and a stimulation generator 98. In addition to the functions of processor 80 described above with respect to FIG. 3, processor 80 in FIG. 4 also may control stimulation generator 98 to deliver stimulation therapy to heart 12 according to a selected one or more therapy programs, which may be stored in memory 82. Specifically, processor 80 may control stimulation generator 96 to deliver electrical waveforms, pulses, trains and sequences of pulses, or shocks with the amplitudes, pulse widths, frequency, or electrode polarities specified by the selected one or more therapy programs.

Stimulation generator 98 is electrically coupled to electrodes 52, 54, 56, 58, 60, 62, 70, 74, 76, 78, e.g., via conductors of the respective lead 42, 44, 46, or, in the case of housing electrode 70, via an electrical conductor disposed within housing 72 of IMD 40. Stimulation generator 98 is configured to generate and deliver electrical stimulation therapy to heart 12. For example, stimulation generator 98 may deliver defibrillation shocks to heart 12 via at least two electrodes 70, 74, 76, 78. Stimulation generator 98 may deliver pacing pulses or waveforms via ring electrodes 52, 56, 60 coupled to leads 42, 44, and 46, respectively, and/or helical electrodes 54, 58, 62 of leads 42, 44, and 46, respectively. In some examples, stimulation generator 98 delivers pacing, cardioversion, or defibrillation stimulation in the form of electrical pulses. In other examples, stimulation generator 98 may deliver one or more of these types of stimulation in the form of other signals, such as sine waves, square waves, or other substantially continuous time signals.

Stimulation generator 98 may include a switch module (not shown) and processor 80 may use the switch module to select, e.g., via a data/address bus, which of the available electrodes are used to deliver defibrillation pulses or pacing pulses. The switch module may include a switch array, switch matrix, multiplexer, or any other type of switching device suitable to selectively couple stimulation energy to selected electrodes.

Processor 80 may include a pacer timing and control module, which may be embodied as hardware, firmware, software, or any combination thereof. The pacer timing and control module may comprise a dedicated hardware circuit, such as an ASIC, separate from other components of processor 80, such as a microprocessor, or a software module executed by a component of processor 80, which may be a microprocessor or ASIC. The pacer timing and control module may include programmable counters which control the basic time intervals associated with DDD, VVI, DVI, VDD, AAI, DDI, DDDR, VVIR, DVIR, VDDR, AAIR, DDIR, DDT, and other modes of single, dual or multi-site chamber pacing. In the aforementioned pacing modes, "D" may indicate dual chamber, "V" may indicate a ventricle, "I" may indicate inhibited pacing (e.g., no pacing), and "A" may indicate an atrium, "R" indicates rate modulation. The first letter in the pacing mode may indicate the chamber that is paced, the second letter may indicate the chamber in which an electrical signal is sensed, the third letter may indicate the chamber in which the response to sensing is provided, the fourth letter "R" indicates the absence (0) or presence of rate modulation. A fifth letter can be used to indicate multi-site pacing.

Intervals defined by the pacer timing and control module within processor 80 may include atrial and ventricular pacing escape intervals, refractory periods during which sensed P-waves and R-waves are ineffective to restart timing of the escape intervals, and the pulse widths of the pacing pulses. As another example, the pace timing and control module may define a blanking period, and provide signals from sensing module 86 to blank one or more channels, e.g., amplifiers, for a period during and after delivery of electrical stimulation to heart 12. The durations of these intervals may be determined by processor 80 in response to stored data in memory 82. The pacer timing and control module of processor 80 may also determine the amplitude of the cardiac pacing pulses or waveforms.

During pacing, escape interval counters within the pacer timing/control module of processor 80 may be reset upon sensing of R-waves and P-waves. The count at the time a ventricular escape interval is reset indicates the pertinent R-R interval at that time. Stimulation generator 98 may include pacer output circuits that are coupled, e.g., selectively by a switching module, to any combination of electrodes 52, 54, 56, 58, 60, 62, 70, 74, 76, 78 appropriate for delivery of a bipolar or unipolar pacing pulse to one of the chambers of heart 12.

Processor 80 may reset the escape interval counters upon the generation of pacing pulses by stimulation generator 98, and thereby control the basic timing of cardiac pacing functions, including anti-tachyarrhythmia pacing.

When IMD 40 is configured to generate and deliver defibrillation shocks to heart 12, stimulation generator 98 may include a high voltage charge circuit and a high voltage output circuit. In the event that generation of a cardioversion or defibrillation shock is required, processor 80 may employ the escape interval counter to control timing of such cardioversion and defibrillation shocks, as well as associated refractory periods. In response to the detection of atrial or ventricular fibrillation of tachyarrhythmia requiring a cardioversion pulse, processor 80 may activate a cardioversion/defibrillation control module, which may, like pacer timing and control module, be hardware component of processor 80 and/or a firmware or software module executed by one or more hardware components of processor 80. The cardioversion/defibrillation control module may initiate charging of the high voltage capacitors of the high voltage charge circuit of stimulation generator 98 under control of a high voltage charging control line.

Processor 80 may monitor the voltage on the high voltage capacitor, e.g., via a voltage charging and potential (VCAP) line. In response to the voltage on the high voltage capacitor reaching a predetermined value set by processor 80, processor 80 may generate a logic signal that terminates charging. Thereafter, timing of the delivery of the defibrillation or cardioversion pulse by stimulation generator 98 is controlled by the cardioversion/defibrillation control module of processor 80. Following delivery of the fibrillation or tachycardia therapy, processor 80 may return stimulation generator 98 to a cardiac pacing function and await the next successive interrupt due to pacing or the occurrence of a sensed atrial or ventricular depolarization.

Stimulation generator 98 may deliver cardioversion or defibrillation pulses with the aid of an output circuit that determines whether a monophasic or biphasic pulse is delivered, whether housing electrode 70 serves as cathode or anode, and which electrodes are involved in delivery of the cardioversion of defibrillation pulses. Such functionality may be provided by one or more switches or a switching module of stimulation generator 98.

Figure 5:
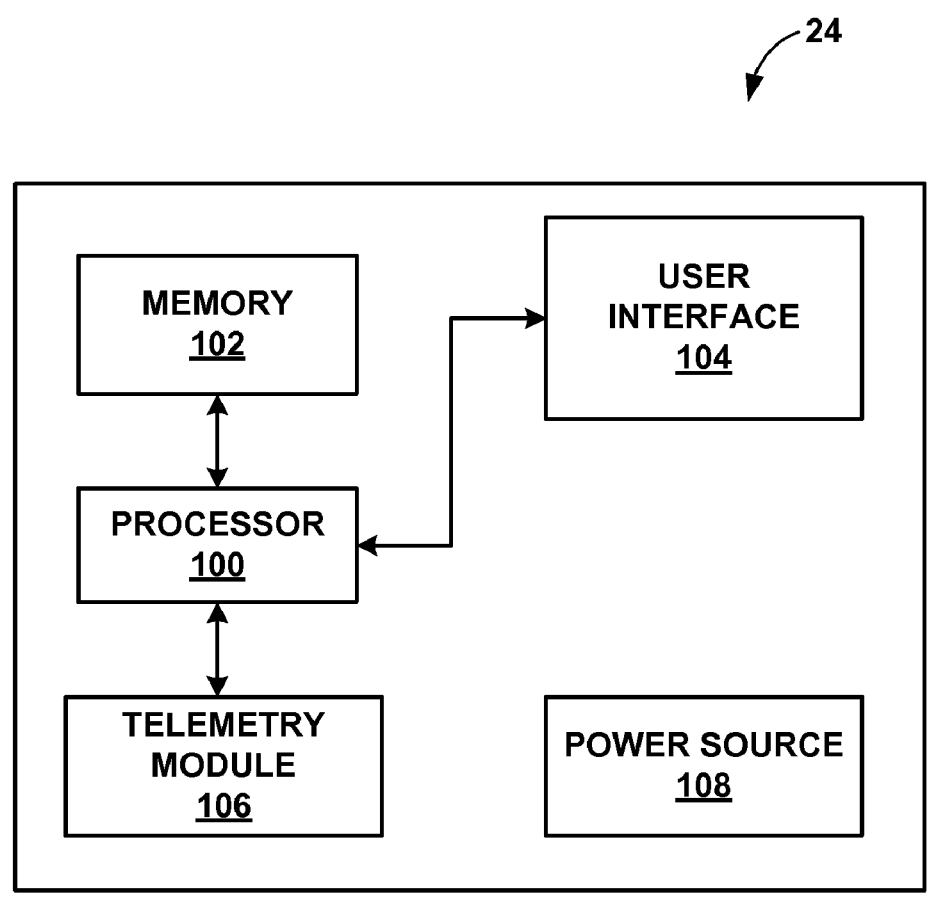
FIG. 5 is a functional block diagram of an example medical device programmer.

In some examples, processor 80 and/or stimulation generator 98 may be responsive to a risk stratification indicator generated by processor 80 or processor 100 of programmer 24 (FIG. 5). In some instances, processor 80 or processor 100 may generate an instruction to initiate or modify a therapy program according to which IMD 40 delivers stimulation to heart 12 based on the risk stratification indicator. For example, the instruction may initiate resetting or suspension of the current therapy program by IMD 40, or may initiate IMD 40 to switch to a different therapy program. Each therapy program may define a plurality of stimulation parameters, including, for example, stimulation pulse width, stimulation pulse amplitude, stimulation frequency, an electrode configuration and/or polarity, or the like. In response to the instruction, processor 80 may control stimulation generator 98 to initiate delivery of stimulation therapy, reset stimulation therapy, cease delivery of stimulation therapy, change one or more therapy program parameters according to which stimulation generator 98 delivers therapy, or otherwise modify stimulation therapy delivered by stimulation generator 98. For example, therapy may be modified to better address a worsening or lessening heart failure condition of patient 14.

FIG. 5 is a functional block diagram of an example programmer 24. As shown in FIG. 5, programmer 24 includes processor 100, memory 102, user interface 104, telemetry module 106, and power source 108. Programmer 24 may be a dedicated hardware device with dedicated software for programming of IMD 16. Alternatively, programmer 24 may be an off-the-shelf computing device running an application that enables programmer 24 to program IMD 16.

A user such as a clinician may use programmer 24 to select therapy programs (e.g., sets of stimulation parameters), generate new therapy programs, modify therapy programs through individual or global adjustments or transmit the new programs to a medical device, such as IMD 40 (FIGS. 2 and 4). The user may also use programmer 24 to program or modify parameters related to the determination of a risk stratification indicator, such as, for example, threshold values to which the HRT measurements are compared, and other patient related parameters such as age, gender, QRS width, LVEF, and SDNN. In some examples, the user may also utilize programmer 24 to modify the frequency or length of detection intervals, the particular perturbation that initiates a detection interval, or the like. The user may interact with programmer 24 via user interface 104, which may include a display to present a graphical user interface to a user, and a keypad or another mechanism for receiving input from a user.

The user may also use programmer 24 to retrieve data stored in memory 82 of IMD 16, 40, such as, for example, physiological parameters sensed by sensors communicatively coupled to IMD 16, 40. The physiological parameters may be used by programmer 24 to compute a risk stratification indicator or other related indicators such as HRT. The user further may use programmer 24 to retrieve a risk stratification indicator stored in memory 82 or an implantation indicator stored in memory 82, if computed within IMD 16, or other measurements or indicators related to the computation of the risk stratification indicator (e.g., HRT measurement), if computed within IMD 16. Hence, the HRT analysis may be performed within IMD 16 or within programmer 24. Likewise, the risk stratification indicator may be computed within IMD 16 or within programmer 24.

Processor 100 can take the form one or more microprocessors, DSPs, ASICs, FPGAs, programmable logic circuitry, or the like, and the functions attributed to processor 100 herein may be embodied as hardware, firmware, software or any combination thereof. Memory 102 may store instructions that cause processor 100 to provide the functionality ascribed to programmer 24 herein, and information used by processor 100 to provide the functionality ascribed to programmer 24 herein.

Memory 102 may include any fixed or removable magnetic, optical, or electrical media, such as RAM, ROM, CD-ROM, hard or floppy magnetic disks, EEPROM, or the like. Memory 102 may also include a removable memory portion that may be used to provide memory updates or increases in memory capacities. A removable memory may also allow patient data to be easily transferred to another computing device, or to be removed before programmer 24 is used to program therapy for another patient. Memory 102 may also store information that controls therapy delivery by IMD 40, such as stimulation parameter values.

Programmer 24 may communicate wirelessly with IMD 40, such as using RF communication or proximal inductive interaction. This wireless communication is possible through the use of telemetry module 106, which may be coupled to an internal antenna or an external antenna. An external antenna that is coupled to programmer 24 may be placed over IMD 16. Telemetry module 106 may be similar to telemetry module 90 of IMD 16, 40 (FIGS. 3 and 4).

Telemetry module 106 may also be configured to communicate with another computing device via wireless communication techniques, or direct communication through a wired connection. Examples of local wireless communication techniques that may be employed to facilitate communication between programmer 24 and another computing device include RF communication according to the 802.11 or Bluetooth specification sets, infrared communication, e.g., according to the IrDA standard, or other standard or proprietary telemetry protocols. In this manner, other external devices may be capable of communicating with programmer 24 without needing to establish a secure wireless connection.

Power source 108 delivers operating power to the components of programmer 24. Power source 108 may include a battery and a power generation circuit to produce the operating power. In some examples, the battery may be rechargeable to allow extended operation. Recharging may be accomplished by electrically coupling power source 108 to a cradle or plug that is connected to an alternating current (AC) outlet. In addition or alternatively, recharging may be accomplished through proximal inductive interaction between an external charger and an inductive charging coil within programmer 24. In other examples, traditional batteries (e.g., nickel cadmium or lithium ion batteries) may be used. In addition, programmer 24 may be directly coupled to an alternating current outlet to power programmer 24. Power source 108 may include circuitry to monitor power remaining within a battery. In this manner, user interface 104 may provide a current battery level indicator or low battery level indicator when the battery needs to be replaced or recharged. In some cases, power source 108 may be capable of estimating the remaining time of operation using the current battery.

In some examples, processor 100 may generate a risk stratification indicator based on a HRT measurement, such as a difference (Δ) in HRT slope over time. Again, the HRT measurement may be obtained from IMD 16 or determined by processor 100 based on raw, processed or parametric data obtained from IMD 16. For example, as described in further detail above, processor 80 of IMD 16, 40 may determine the HRT slope based on R-R interval differences. Processor 80 then may communicate the HRT measurements to processor 100 via telemetry modules 90 and 106. Processor 100 may generate the risk stratification indicator based on the HRT measurements. Additionally, an age of patient 14, gender, history of heart failure or other concomitant diseases, and other cofounders such as diabetes, hypertension, hypercholesterolemia, or measurable parameters as QRS width, LVEF, SDNN or the like may be used to by processor 100 to generate the risk stratification indicator.

In other examples, processor 100 of programmer 24 also may determine the HRT measurement based on raw or parametric signal data communicated from processor 80 to processor 100 via telemetry modules 90 and 106. For example, processor 80 may detect cardiac signals via one or more of electrodes 52, 54, 56, 58, 60, 62, 70, 74, 76, 78. Processor 80 may transfer the cardiac signals to processor 100 via telemetry modules 90 and 106. Processor 100 may apply one or more techniques described in this disclosure to determine the HRT measurements based on the cardiac signals. Processor 100 then may generate the risk stratification indicator based on the HRT measurement. In some examples, processor 100 may generate the risk stratification indicator based on the HRT measurements and an age of patient 14, gender of patient 14, history of heart failure or cardiac disease of patient 14, or the like.

Processor 100 may also generate an indicator based on the risk stratification indicator. The indicator may include, for example, an implantation indicator, which indicates the patient is a candidate for implantation of an implantable therapy device, such as an implantable cardioverter/defibrillator (ICD), or an implantable drug delivery device. Processor 100 may also automatically initiate, cease, or adjust an existing cardiac therapy delivered by IMD 40 based on the risk stratification indicator. In other examples, processor 100 may generate an alert or alarm to a user, such as patient 14 or a clinician. The alert or alarm may indicate that a condition of patient 14 has changed or is changing.

Figure 6:
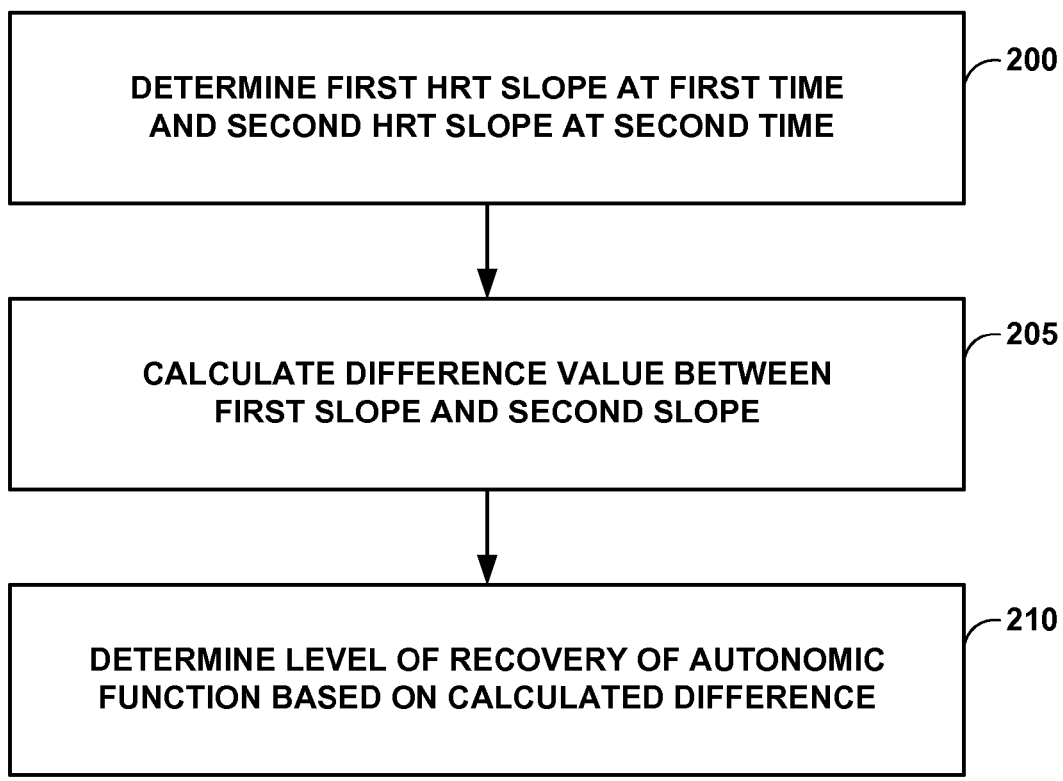
FIG. 6 is a flow diagram illustrating an example technique of generating a risk stratification indicator.

FIG. 6 is a flow diagram illustrating an example technique of generating a risk stratification indicator. Although IMD 16 or IMD 40 may perform the technique illustrated in FIG. 6, IMD 16 will be described for purposes of illustration. As shown in FIG. 6, IMD 16 and, in particular, a processor, e.g., processor 80, determines physiological parameters of a patient such as a first HRT slope, i.e., turbulence slope, at a first time, e.g., 3 days to 21 days, more preferably 5 days to 14 days, and even more preferably about 7 days after the myocardial infarction, and a second HRT slope, i.e., turbulence slope, at a second time, e.g., 4 weeks to 10 weeks, more preferably 5 weeks to 8 weeks, and even more preferably about 6 weeks after the myocardial infarction, or about 5 weeks after the first time (200). The slope is measured over time intervals, e.g., 24 hours, which are generally coincident with the first and second times. In some examples, cardiac sensing module 86 may first sense the physiological signals of the patient and processor 80 may process the physiological signals to transform the signals into physiological parameters. Then, processor 80, for example, calculates a difference value between the first slope and the second slope (205). The difference value may be expressed as change (Δ) in HRT slope. Based on the calculated difference, processor 80 determines a level of recovery of autonomic function (210). In some examples, the calculated difference may be compared to a threshold value, such that determining a level of recovery includes determining a level of recovery based on the comparison. For example, if the difference between the first slope and the second slope is equal to or greater than a threshold value, e.g., about 2 ms per R-R interval, the patient's autonomic function, or level of recovery, may be determined to be in a first category, e.g., recovering satisfactorily, and, as such, the patient is not at risk. In some examples, multiple thresholds may be used in order to provide different levels of risk stratification. If, however, the difference between the first slope and the second slope is less than about 2 ms per R-R interval, the patient's autonomic function, or level of recovery, may be determined to be in a second category, e.g., recovering unsatisfactorily, and, as such, the patient is at risk. In some examples, processor 80 may generate a risk stratification indicator, e.g., a binary value, if the level of recovery is determined to be unsatisfactory. In one example, a processor of an IMD, e.g., IMD 16, may generate the risk stratification indicator. In some examples, the IMD may transmit the risk stratification indicator from the IMD to another device, e.g., programmer 24. In some examples, the risk stratification indicator may indicate one or more of the following: that the patient should be hospitalized, that the patient should be fitted with an implantable therapy device configured to deliver therapy, and that therapy delivered to the patient (e.g., cardiac therapy, spinal cord stimulation (SCS), and other types of neuro-modulation therapy) should be modified. In one example, therapy includes one of electrical stimulation or drug delivery.

The following paragraph describes steps 200-210 in more detail: (1) At 1 week (about seven days) following a myocardial infarction, perform for a period of 24 hours the following steps:
  a. Derive from EGM signal the timing of heartbeat events and calculate the intervals between two subsequent heartbeat events.
  b. Identify premature ventricular contractions (PVCs) in the stream of heartbeat events by:
    i. Flagging an event recorded on the Ventricular channel after sequence with no intervening p-wave on the atrial channel, (a p-R-PVC sequence), and/or
    ii. by looking at the temporal behavior of the events (for example, the interval associated with the PVC event is shorter compared to the preceding normal intervals and the interval following the PVC is longer compared to the preceding normal intervals), and/or
    iii. by changes of heartbeat morphology in the EGM compared to normal beats.
  c. When a PVC is identified, collect a plurality of R-R intervals, e.g., fifteen, following the longer R-R interval after the PVC.
  d. When all fifteen collected R-R intervals are derived from normal heartbeat events, store these R-R intervals in memory.

(2) After collecting the R-R interval data for 24 hours, calculate the average interval for each interval bin in order to generate fifteen averaged intervals.

(3) Using the averaged fifteen intervals, calculate over any five consecutive intervals the slope of a linear regression line and store the maximum positive slope value as max-slope-7.

(4) If in step (1) no PVC followed by fifteen normal R-R intervals was identified, repeat steps (1)-(3) for another six days until at least one suitable PVC is identified. If no suitable PVC is found after the additional six days, store INVALID_VALUE in max-slope-7 and proceed to step (8).

(5) At 6 weeks (about 42 days) after the myocardial infarction, repeat steps (1)-(4). Store the maximum positive slope value as max-slope-42 and, if no suitable PVC was found at day 42, repeat the processing until a period of 24 hours contains at least one suitable PVC.

(6) As soon as valid max-slope-7 and max-slope-42 values are available, calculate the difference between these two values and store the difference as diff-slope.

(7) If the value diff slope is lower than 2.0, set the alarm flag to 1, otherwise set the alarm flag to 0.

(8) If no valid values for max-slope-7 or max-slope-42 are available, set the alarm flag to 0.

Figure 7:
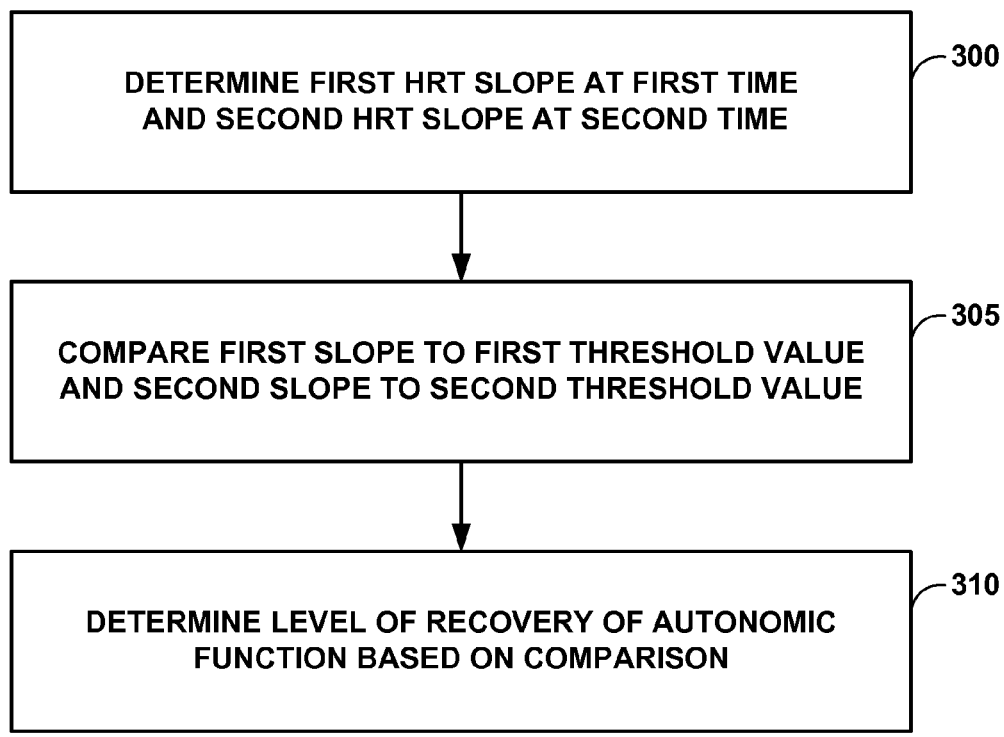
FIG. 7 is a flow diagram illustrating another example technique of generating a risk stratification indicator.

FIG. 7 is a flow diagram illustrating another example technique of generating a risk stratification indicator. In the method shown in FIG. 7, IMD 16 and, in particular, a processor, e.g., processor 80, determines a first HRT slope, i.e., turbulence slope, at a first time, e.g., 3 days to 21 days, more preferably 5 days to 14 days, and even more preferably about 7 days after the myocardial infarction, and a second HRT slope, i.e., turbulence slope, at a second time, e.g., 4 weeks to 10 weeks, more preferably 5 weeks to 8 weeks, and even more preferably about 6 weeks after the myocardial infarction (300). Processor 80 then compares the first HRT slope to a first threshold value and the second HRT slope to a second threshold value (305). In one example, the first threshold value and the second threshold value are the same threshold value. In another example, the first threshold value and the second threshold value are different threshold values. In some examples, the first threshold value and the second threshold values may be about 2.5 ms per R-R interval. In other examples, the first threshold value may be in a range between about 1.5 ms per R-R interval and 2.5 ms per R-R interval, and the second threshold value may be in a range between about 3 ms per R-R interval and 3.5 ms per R-R interval. Based on the comparison, processor 80 determines a level of recovery of autonomic function (310). For example, if the first slope is equal to or greater than the first threshold value, and the second slope is equal to or greater than the first threshold value and/or a second threshold value, the patient's autonomic function is recovering satisfactorily and, thus, the patient is not at risk. If, however, the first slope is less than the first threshold value, and the second slope is less than the first threshold value and/or a second threshold value, the patient's autonomic function is not recovering satisfactorily and, as such, the patient is at risk. In some examples, processor 80 may generate a risk stratification indicator, e.g., a binary value, if the level of recovery is determined to be unsatisfactory. In one example, a processor of an IMD, e.g., IMD 16, may generate the risk stratification indicator. In some examples, the IMD may transmit the risk stratification indicator from the IMD to another device, e.g., programmer 24. In some examples, the risk stratification indicator may indicate that the patient should be hospitalized and/or that the patient should be fitted with an implantable therapy device configured to deliver electrical stimulation.

Figure 8:
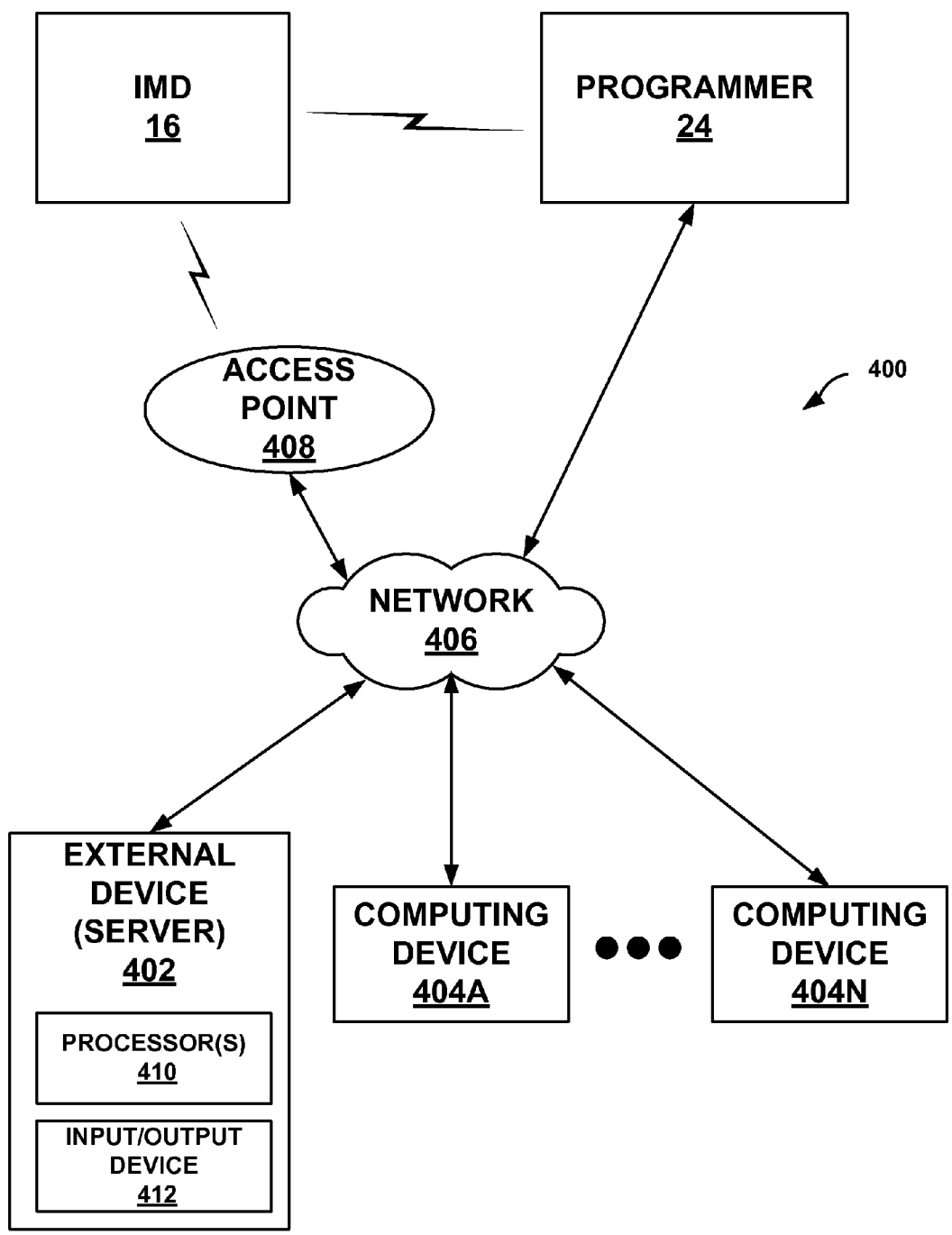
FIG. 8 is a block diagram illustrating an example system that includes an external device, such as a server, and one or more computing devices that are coupled to the IMD and programmer shown in FIG. 1 via a network.

FIG. 8 is a block diagram illustrating an example system 400 that includes an external device, such as a server, and one or more computing devices that are coupled to the IMD and programmer shown in FIG. 1 via a network. In some implementations, physiological signal data may be transmitted from IMD 16 or 40 to programmer 24 or another device and, in turn, to a server and/or client computers coupled to programmer 24 or the other device via a network. In this case, a remote server may compute HRT measurements and/or compute a risk stratification indicator based on information received from IMD 16 or 40 and/or programmer 24. Alternatively, HRT measurements and/or risk stratification indicators generated by IMD 16 or 40 or programmer 24 may be transmitted to such a remote server or client computer for processing, archival and/or viewing by a clinician or other caregiver.

In the example of FIG. 8, example system 400 includes an external device, such as a server 402, and one or more client computing devices 404A-404N, that are coupled to the IMD 16 and programmer 24 shown in FIG. 1 via a network 406. In this example, IMD 16 may use its telemetry module 90 to communicate with programmer 24 via a first wireless connection, and to communicate with an access point 408 via a second wireless connection. In the example of FIG. 8, access point 408, programmer 24, server 402, and computing devices 404A-404N are interconnected, and able to communicate with each other, through network 406.

In some cases, one or more of access points 408, programmer 24, server 402, and computing devices 404A-404N may be coupled to network 406 through one or more wireless connections. IMD 16, programmer 24, server 402, and computing devices 404A-404N may each comprise one or more processors, such as one or more microprocessors, DSPs, ASICs, FPGAs, programmable logic circuitry, or the like, that may perform various functions and operations, such as those described herein. For example, as illustrated in FIG. 8, server 402 may comprise one or more processors 410 and an input/output device 412, which need not be co-located.

Server 402 may, for example, implement any of the methods described in this disclosure for generation of a risk stratification indicator, including generation of the risk stratification indicator itself and any intermediate operations, such as generating HRT indicators from raw, processed or parametric cardiac signals, marker channel data, or other information. Server 402 also may provide a database or other memory for storing such information.

Access point 408 may comprise a device that connects to network 406 via any of a variety of connections, such as telephone dial-up, digital subscriber line (DSL), optical fiber or cable modem connections. In other examples, access point 408 may be coupled to network 406 through different forms of connections, including wired or wireless connections. In some examples, access point 408 may be co-located with patient 14 and may comprise one or more programming units and/or computing devices (e.g., one or more monitoring units) that may perform various functions and operations described herein. For example, access point 408 may include a home-monitoring unit that is co-located with patient 14 and that may monitor the activity of IMD 16. In some examples, server 402 or one or more of the computing devices 404A-404N may perform any of the various functions or operations described herein.

Network 406 may comprise a local area network, wide area network, or global network, such as the Internet. In some cases, programmer 24 or server 402 may assemble HRT risk stratification indicators or data in web pages or other documents for viewing by trained professionals, such as clinicians, via viewing terminals associated with computing devices 404A-404N. System 400 may be implemented, in some aspects, with general network technology and functionality similar to that provided by the Medtronic CareLink® Network developed by Medtronic, Inc., of Minneapolis, Minn.

The techniques described in this disclosure, including those attributed to IMD 16 or various constituent components, may be implemented, at least in part, in hardware, software, firmware or any combination thereof. For example, various aspects of the techniques may be implemented within one or more processors, including one or more microprocessors, digital signal processors (DSPs), application specific integrated circuits (ASICs), field programmable gate arrays (FPGAs), or any other equivalent integrated or discrete logic circuitry, as well as any combinations of such components, embodied in programmers, such as physician or patient programmers, stimulators, or other devices. The term "processor" or "processing circuitry" may generally refer to any of the foregoing circuitry, alone or in combination with other circuitry, or any other equivalent circuitry.

Such hardware, software, or firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

When implemented in software, the functionality ascribed to the systems, devices and techniques described in this disclosure may be embodied as instructions on a computer-readable medium such as random access memory (RAM), read-only memory (ROM), non-volatile random access memory (NVRAM), electrically erasable programmable read-only memory (EEPROM), FLASH memory, magnetic data storage media, optical data storage media, or the like. The instructions may be executed to support one or more aspects of the functionality described in this disclosure.

Various examples have been described. These and other examples are within the scope of the following claims.

The invention claimed is:

1. A method comprising:
   determining, by one or more processors and based on physiological parameters of a patient obtained by an implantable medical device, a first heart rate turbulence (HRT) slope at a first time after an occurrence of a myocardial infarction and a second HRT slope at a second time after the occurrence of the myocardial infarction;
   calculating, by the one or more processors, a difference value between the first HRT slope and the second HRT slope; and
   determining, by the one or more processors, a level of recovery of autonomic function between the first time and the second time based on the calculated difference.

2. The method of claim 1, wherein the first time is approximately one week after the occurrence of the myocardial infarction, and wherein the second time is approximately six weeks after the occurrence of the myocardial infarction.

3. The method of claim 1, further comprising:
   comparing the difference value to a threshold value of about 2 milliseconds per R-R interval, wherein determining a level of recovery comprises determining the level of recovery based on the comparison.

4. The method of claim 3, wherein determining the level of recovery of autonomic function based on the calculation comprises:
   determining the level of recovery to be in a first category if the difference value is equal to or greater than the threshold value; and
   determining the level of recovery to be in a second category if the difference value is less than the threshold value.

5. The method of claim 4, further comprising:
   generating a risk stratification indicator if the level of recovery is determined to be in the second category.

6. The method of claim 5, wherein the risk stratification indicator indicates at least one of that the patient should be hospitalized, that the patient should be fitted with an implantable therapy device configured to deliver therapy, and that therapy delivered to the patient should be modified.

7. The method of claim 1, further comprising:
   delivering, when no intrinsic abnormal heartbeats are occurring, electrical stimulation at a first time in order to induce a plurality of abnormal heartbeats at the first time; and
   delivering, when no intrinsic abnormal heartbeats are occurring, electrical stimulation at a second time in order to induce abnormal heartbeats at the second time,
   wherein determining, from physiological parameters of a patient, a first heart rate turbulence (HRT) slope at a first time and a second HRT slope at a second time comprises determining the first HRT slope from the abnormal heartbeats induced at the first time and determining the second HRT slope from the abnormal heartbeats induced at the second time.

8. An implantable medical device (IMD) comprising:
   a measurement unit configured to obtain physiological parameters for a patient; and
   a processor configured to:
      determine, from the physiological parameters, a first heart rate turbulence (HRT) slope at a first time after an occurrence of a myocardial infarction and a second HRT slope at a second time after the occurrence of the myocardial infarction;

calculate a difference value between the first HRT slope and the second HRT slope; and determine a level of recovery of autonomic function based on the calculated difference.

9. The IMD of claim 8, wherein the first time is approximately one week after the occurrence of the myocardial infarction, and wherein the second time is approximately six weeks after the occurrence of the myocardial infarction.

10. The IMD of claim 8, wherein the processor is further configured to:

compare the difference value to a threshold value of about 2 milliseconds per R-R interval, and wherein the processor configured to determine a level of recovery is further configured to determine the level of recovery based on the comparison.

11. The IMD of claim 10, wherein the processor configured to determine the level of recovery of autonomic function based on the calculation is further configured to:

determine the level of recovery to be in a first category if the difference value is equal to or greater than the threshold value; and determine the level of recovery to be in a second category if the difference value is less than the threshold value.

12. The IMD of claim 11, wherein the processor is further configured to:

generate a risk stratification indicator if the level of recovery is determined to be in the second category.

13. The IMD of claim 12, further comprising:

transmitting the risk stratification indicator from the IMD to another device.

14. The IMD of claim 13, wherein the risk stratification indicator indicates at least one of that the patient should be hospitalized, that the patient should be fitted with an implantable therapy device configured to deliver therapy, and that therapy delivered to the patient should be modified.

15. A system comprising:

an implantable medical device (IMD) configured to obtain physiological parameters for a patient; and an external computing device configured to:

receive the physiological parameters;

determine, from the physiological parameters, a first heart rate turbulence (HRT) slope at a first time after an occurrence of a myocardial infarction and a second HRT slope at a second time after the occurrence of the myocardial infarction;

calculate a difference value between the first HRT slope and the second HRT slope; and determine a level of recovery of autonomic function based on the calculated difference.

16. The system of claim 15, wherein the first time is approximately one week after the occurrence of the myocardial infarction, and wherein the second time is approximately six weeks after the occurrence of the myocardial infarction.

17. The system of claim 15, wherein the external computing device is further configured to:

compare the difference value to a threshold value of about 2 milliseconds per R-R interval, and wherein the external computing device is further configured to determine a level of recovery is further configured to determine the level of recovery based on the comparison.

18. The system of claim 17, wherein the external computing device configured to determine the level of recovery of autonomic function based on the calculation is further configured to:

determine the level of recovery to be in a first category if the difference value is equal to or greater than the threshold value; and determine the level of recovery to be in a second category if the difference value is less than the threshold value.

19. The system of claim 18, wherein the external computing device is further configured to:

generate a risk stratification indicator if the level of recovery is determined to be in the second category.

20. The system of claim 19, wherein the risk stratification indicator indicates at least one of that the patient should be hospitalized, that the patient should be fitted with an implantable therapy device configured to deliver therapy, and that therapy delivered to the patient should be modified.

* * * * *